United States Patent [19]

Horder et al.

[11] Patent Number: 4,842,866
[45] Date of Patent: Jun. 27, 1989

[54] SLOW RELEASE SOLID PREPARATION

[75] Inventors: Rodney Horder, Sittingbourne; Michael Banks, Herne Bay; Thomas H. Hoadley, Sheppey, all of England

[73] Assignee: Abbott Laboratories Ltd., Queenborough, England

[21] Appl. No.: 132,678

[22] Filed: Dec. 14, 1987

Related U.S. Application Data

[63] Continuation of Ser. No. 818,443, Jan. 10, 1986, abandoned.

[30] Foreign Application Priority Data

Jan. 11, 1985 [EP] European Pat. Off. ......... 85300215.2

[51] Int. Cl.$^4$ .......................... A61K 9/22; A61K 9/26
[52] U.S. Cl. .................................... 424/468; 424/469; 424/470; 424/485; 424/488; 424/499; 424/500
[58] Field of Search ............... 424/468, 469, 470, 485, 424/488, 499, 500

[56] References Cited

U.S. PATENT DOCUMENTS 3,640,741 2/1972 Etes ..................................... 106/170

FOREIGN PATENT DOCUMENTS 188040 7/1986 European Pat. Off. .
985218 7/1951 France .
51-76413 7/1976 Japan .
51-76415 7/1976 Japan .
1355985 6/1974 United Kingdom .

OTHER PUBLICATIONS

C. A. 105(4): 120807b (1986), of EPO 188040 July 23, 1986, Horder et al.
A. E. Abotaleb et al., Pharmazie 38 473 (1983), Discloses Sodium Calcium Alginate as a Disintegrating Agent in Pharmaceutical Tablets.
E. Shotton et al., J. Pharm. Sci. 65 1170 (1976), Discloses Sodium Calcium Alginate as a Disintegrating Agent in Pharmaceutical Tablets.
K. A. Khan et al., J. Pharm. Sci. 64 166 (1975), Discloses Sodium Calcium alginate as a Disintegrating Agent in Pharmaceutical Tablets.
N.-C. Hai et al., Yao Hsueh Tung Pao. 16(3), 59–60 (1981) [Chem. Abstr., 95:1385461], Discloses Calcium Alginate as a Component of a Drug Delivery Matrix.
M. Jacob et al., Pharm. Acta Helv. 54 44 (1979), Discloses Sodium Calcium Alginate as an Excipient in a Pharmaceutical Tablet.

Primary Examiner—Shep K Rose
Attorney, Agent, or Firm—Steven F. Weinstock; Steven R. Crowley

[57] ABSTRACT

A controlled, slow release, solid pharmaceutical preparation includes at least one active ingredient and a blend of sodium alginate and sodium-calcium alginate.

10 Claims, No Drawings

SLOW RELEASE SOLID PREPARATION

TECHNICAL FIELD

This is a continuation of co-pending application Ser. No. 818,443, filed on Jan. 10, 1986, now abandoned.

The invention relates to a controlled slow release solid preparation formulation which comprises sodium-calcium alginate.

BACKGROUND ART

It is well known to prepare slow release tablets utilizing an algin gel. Typically, a water soluble alginate such as sodium alginate and calcium ions in the form of a calcium salt are reacted to gelatinize the algin by converting it into an insoluble calcium alginate gel. On the addition of a strong acid to the mixture of sodium alginate and calcium salt, calcium salt is slowly ionized to yield calcium ions. The calcium ions then react with the soluble alginate to form an insoluble calcium alginate. Gelation proceeds through gradual ionization of the calcium salt. With these formulations, the controlled release properties of the alginate gel have been varied by varying the molecular weight of alginate, the alginate concentration, the type of polyvalent cation cross-linking agent or the concentration of the cation.

Exemplary of the prior art is Great Britain Pat. No. 1,355,985 which discloses a solid slow release preparation for prolonged drug action, the preparation containing a mixture of sodium alginate and a slightly soluble calcium salt which, when in contact with gastric juices, liberates calcium ions. The calcium ions react with sodium alginate to form a sponge-like gel of calcium alginate through which a drug slowly diffuses. The gel is formed by calcium ions cross-linking with a water soluble alginate and has a lattice mesh through which water is absorbed. Inert, insoluble ingredients may be added to control the porosity of the lattice mesh. The lattice retards the apparent dissolution of the active ingredient.

The sodium alginate formulations with calcium ions known to date have been unsuccessful in providing the controllable and reproducible release of drugs presumably due top the unpredictable nature of the reactivity of the calcium ions resulting in poorly formed gels and due to the periodic precipitation of insoluble materials into the gastrointestinal tract.

Other references which may be pertinent to the present invention include U.S. Pat. No. 3,640,741 which discloses a plastic mass containing a gel for the slow release of pharmaceuticals. The gel is made by mixing calcium chloride and sodium alginate in a glycol solution containing a pharmaceutical. Similarly Japanese Pat. Nos. 76415 and 76413 disclose the use of sodium alginate in solid pharmaceutical formulations. Lastly, numerous references including A. E. Abotaleb et al., Pharmazie, 38,473 (1983)); E. Shotton et al., *J. Pharm. Sci.* 65, 1170 (1976); and K. A. Khan et al., *J. Pharm. Sci.* 64, 166 (1975), all disclose the use of sodium calcium alginate, which is a 50:50 physical mixture of sodium alginate and calcium alginate, in pharmaceutical tablets as disintegrating agents.

In spite of the above-noted prior art, no known pharmaceutical tablet formulation to date provides controllable, extended release profiles up to twenty four (24) hours and, particularly, where an active drug ingredient exceeds 50% by weight of the solid preparation. Such a preparation would enable once daily dosing to fulfil, e.g., geriatric patient compliance for daily drug administration.

DISCLOSURE OF THE INVENTION

In accordance with the invention a controlled, slow release, solid preparation comprises at least one active ingredient, sodium alginate and sodium-calcium alginate. The preparation may further comprise binding, bulking, lubricating and coloring agents, as needed, and may be coated with materials not specifically designed for control or modification of drug release.

Any active ingredient(s) is acceptable, but is preferably selected from pharmaceuticals which because of rapid elimination or metabolism are necesary to be administered frequently within a twenty four (24) hour period; e.g. buflomedil hydrochloride (vasodilator), tulobuterol hydrochloride (bronchodilator). The invention is particularly advantageous when large dose drugs are desired to be formulated in a controlled release preparation with quantities up to 70% by weight of the active ingredient relative to the solid preparation.

While sodium alginate is normally employed in the practice of this invention, the sodium cation may be replaced by another cation, e.g. potassium or other alkali metals, magnesium, or ammonium to yield a soluble alginate salt. Thus, the alginate could also be, for example, potassium alginate or ammonium alginate.

The sodium-calcium alginate, unlike that used in the prior art, is a sodium-calcium complex salt of alginic acid in which the amount of calcium is precisely controlled, and which is self gelling without the necessity of reacting with the stomach acid or additional calcium ions. While sodium-calcium alginate is normally employed in the practice of this invention, the sodium cation may be replaced by another cation that yields a soluble alginate salt, e.g. potassium or other alkali metals, magnesium, or ammonium; and the calcium cation could be replaced by another polybasic cation (except for magnesium) that yields an insoluble alginate salt, e.g. strontium, iron, barium.

The most preferable preparations described herein typically include sodium alginate, for example, that manufactured and sold by Alginate Industries, Ltd., England, under the trademark "Manucol", and sodium-calcium alginate manufactured and sold by Kelco Division of Merck and Co., Inc., San Diego, Calif., U.S.A., under the trademark "Kelset".

Other ingredients usually used in a preparation in accordance with the invention may include diluents, e.g. starch or microcrystalline cellulose; binders such as starch, polyvinyl pyrrolidone (povidone), sodium carboxymethylcellulose and the like; glidants or lubricants, such as magnesium stearate; bulking agents such as lactose; and approved coloring agents.

The preparation may be processed into tablets, suppositories or used for filing capsules. The preparation may also be coated when desired, for example, to mask an otherwise bitterly tasting preparation.

A pharmaceutical preparation in accordance with the invention having protracted activity when orally administered is normally capable of releasing about 50% of the active ingredient(s) within the first five (5) hours after administration. The remainder of the active ingredient(s) is released gradually within the following 5-10 hours.

In order to illustrate the manufacture of a preparation as described above, reference is made to the following examples, which are not meant to limit the invention in any respect.

EXAMPLES A–L

For each of Examples A–L, the materials indicated in Tables I and II for each example, were processed as follows:

Buflomedil hydrochloride or tulobuterol hydrochloride, sodium alginate, sodium-calcium alginate, and povidone were mixed together; water was added, and the mixture then massed and dried at 50°–60° C. The dried granulation was screened, then mixed with magnesium stearate and compressed into tablets using conventional machinery.

Examples A–D show the retardant effect of increasing the quantity of sodium-calcium alginate while keeping the quantity of sodium alginate constant. Examples E–G show the ability to change the release rate/time profile by varying the total quantity of alginates present but with a constant ratio of sodium alginate to sodium-calcium alginate.

TABLE I

| Ingredients (mg/tablet) | A | B | C | D | E | F | G |
|---|---|---|---|---|---|---|---|
| Buflomedil Hydrochloride | 600 | 600 | 600 | 600 | 600 | 600 | 600 |
| Sodium-Calcium Alginate | 26 | 52 | 100 | 150 | 80 | 150 | 107 |
| Sodium Alginate | 400 | 400 | 400 | 400 | 160 | 300 | 213 |
| Povidone | 40 | 40 | 40 | 40 | 30 | 40 | 30 |
| Magnesium Stearate | 5 | 5 | 6 | 5 | 4–5 | 5 | 5 |

| Time | In-vitro Dissolution % Dose Released (USP XX½) ||||||||
|---|---|---|---|---|---|---|---|
| 1 Hour | 13 | 14 | 10 | 12 | 22 | 11 | 15 |
| 2 Hours | 25 | 24 | 19 | 19 | 29 | — | 24 |
| 4 Hours | 48 | 45 | 34 | 33 | 46 | 33 | 41 |
| 6 Hours | 72 | 65 | 50 | 47 | 61 | — | 56 |
| 8 Hours | 92 | 78 | 64 | 59 | 75 | 58 | 68 |
| 10 Hours | 102 | — | 81 | 71 | 86 | 69 | — |
| 12 Hours | — | — | 93 | 82 | 96 | 79 | 92 |
| 16 Hours | — | — | 97 | — | 95 | — | — |

TABLE II

| Ingredients (mg/tablet) | H | J | K | L |
|---|---|---|---|---|
| Tulobuterol Hydrochloride | 4 | 4 | 6 | 6 |
| Sodium-Calcium Alginate | 200 | 200 | 125 | 75 |
| Sodium Alginate | 200 | 400 | 125 | 75 |
| Povidone | 30 | 60 | 19 | 15 |
| Lactose | 206 | 396 | 200 | 200 |
| Magnesium Stearate | 5 | 10 | 2 | 2 |

| Time (hrs) | In-vitro Dissolution % Dose Released (USP XX½) ||||
|---|---|---|---|---|
| 1 | 5 | 9 | 4 | 7 |
| 2 | 13 | 17 | 10 | 18 |
| 4 | 27 | — | 28 | 41 |
| 6 | 46 | 64 | — | — |
| 8 | 64 | 89 | 64 | 90 |
| 10 | 85 | — | — | — |
| 12 | 103 | — | 98 | — |

Tablets prepared according to the invention may be coated using semisynthetic cellulosic film-forming materials without significant changes to the percentage drug released/time profiles. For example, a coating consisting of hydroxypropyl methylcellulose, polyethylene glycol and approved coloring agents such as water soluble dyes or aluminium lakes applied to the tablet of Example E resulted in the substantially identical release rates shown in Table III.

TABLE III

| Time (hr) | In-vitro Dissolution % Dose Released (USP XX½) |
|---|---|
| 1 | 21 |
| 2 | 30 |
| 4 | 48 |
| 6 | 63 |
| 8 | 75 |
| 10 | 85 |
| 12 | 95 |

Examples in accordance with the teachings of the prior art, sodium alginate - calcium ion formulations, were made to test and compare the dissolution of the resultant preparation with those of the present invention. The results of the testing are shown in Table IV which clearly demonstrates the unexpected, superior sustained release profiles of preparations in accordance with the invention relative to the prior art.

The materials of the formulation included as follows:

| Ingredient (mg/tablet) | EXAMPLE M | EXAMPLE N |
|---|---|---|
| Buflomedil hydrochloride | 600 mg | 175 mg |
| Sodium alginate | 60 mg | 105 mg |
| Calcium hydrogen phosphate | 420 mg | 735 mg |
| Magnesium stearate | 20 mg | 35 mg |
| Titanium dioxide | 100 mg | 175 mg |

EXAMPLE M

Sodium alginate, calcium hydrogen phosphate, magnesium stearate and titanium dioxide were thoroughly blended together and buflomedil hydrochloride was added. Satisfactory tablet compacts could not be made by conventional methods so the blend was massed with water, dried at 50° C. and then compressed on conventional machinery.

EXAMPLE N

In order to overcome the inability to make compacts without wet massing, the amount of buflomedil hydrochloride added to the preparation was reduced. Sodium alginate, calcium hydrogen phosphate, magnesium stearate and titanium dioxide were thoroughly blended together and buflomedil hydrochloride was added to the blend in various concentrations. The above-noted formula was the maximum possible loading of buflomedil hydrochloride that would form a compact suitable for dissolution testing. This compaction was only possible by using exceptionally high pressures on a hand-operated hydraulic press with vacuum assistance to degas the powder bed while under compression.

TABLE IV

| | In-vitro dissolution % dose released (USP XX½) |||||
|---|---|---|---|---|---|
| | EXAMPLE M || EXAMPLE N | EXAMPLE E ||
| | Water | Acid* | Acid* | Water | Acid* |
| 1 hr | 40 | 40 | 29 | 12 | 21 |
| 2 hr | 48 | 61 | 49 | 22 | 30 |
| 3 hr | 56 | 68 | 56 | 33 | 37 |
| 4 hr | 62 | 74 | 63 | 43 | 44 |
| 5 hr | — | — | 68 | — | — |
| 6 hr | 75 | 82 | — | 62 | 58 |

*Test to simulate the effect of gastric acid by immersion of the tablets in an acidic medium for one hour followed by transfer to purified water for the remainder of the test period.

The Examples A–N were tested for in-vitro dissolution (the results of which are shown in Tables I–IV) in accordance with the United States Pharmacopeia XXI, method 2, wherein six tablets were tested individually by immersion in 900 ml of test medium maintained at 37° C. and stirred by a paddle rotating at 60 rpm for buflomedil hydrochloride tablets and at 50 rpm for tulobuterol hydrochloride tablets. Samples of test medium were removed at intervals and assayed for drug content from which percentage release at each time were calculated. Distilled water was used as the dissolution medium throughout except where otherwise indicated. Values in excess of 100% of dose released may be observed as a result of allowable tolerances in tablet manufacture and testing.

It is clearly seen from the above tables that preparations A–L have significantly improved sustained release profiles relative to the prior art preparations, Examples M–N, and can sustain the release of an active ingredient in a wide variety of formulations. Moreover, Examples A–G show that the invention has a greater capacity for active ingredient than as seen in the prior art (e.g. Example N).

The mechanism of release of the active ingredient from the solid preparation is associated with the ability of the preparation, upon exposure to the aqueous medium of gastric juice, to hydrate (absorb water) and swell radially (and not decompose) to produce a viscous gel. Molecules of the active ingredient then migrate to the surface of the gel at the periphery of the preparation by diffusion. The active ingredient is released at a rate corresponding to the rate of hydration of the preparation and the rate of diffusion of the active ingredient. Although it is not clear, it is theorized that hydration of sodium alginate is retarded by the presence of sodium-calcium alginate, or the viscosity of sodium alginate is increased by complexation with sodium-calcium alginate, thereby decreasing the diffusion of active ingredient. Thus, the release rate profile of a solid preparation is controllably and reproducibly varied by altering the ratio of sodium alginate to sodium-calcium alginate blend and the total amount of combined alginates utilized relative to the active ingredient. Further, since there are no insoluble materials included, formed or precipitated out of the preparation, no unfavorable retention of the preparation in the gastrointestinal tract takes place.

In summary, the novel preparations in accordance with this invention provide not only extended release formulations, but extended release formulations that provide a means to precisely control the release of a variety of active ingredients and dosage amounts. Further, the dose of the active ingredient has been found to provide therapeutically effective amounts of active ingredient sustained over a twenty four hour period.

Lastly, the solid preparation is less likely to be retained for an excessive period of time in the gastrointestinal tract since, unlike the prior art, no insoluble materials are precipitated out or included in the formulation.

The slow release preparations in accordance with the invention have been exemplified with pharmaceutical active ingredients hereinabove, the invention can be used in all fields in which active ingredients have pharmaceutical, bactericidal, fungicidal, etc., properties are required to exhibit prolonged activity.

The foregoing specification including the examples and formulation are merely illustrative of the invention. Variations and changes which are obvious to one skilled in the art are intended to be within the scope and nature of the invention which are defined in the appended claims.

We claim:

1. A controlled, slow release, solid preparation comprising sodium alginate, sodium-calcium alginate and a therapeutically effective amount of at least one active ingredient.

2. The preparation of claim 1 further comprising lubricating, bulking, and binding agents.

3. The preparation of claim 1 in tablet form.

4. The preparation of claim 1 wherein the active ingredient is a pharmaceutical exceeding 50% by weight of the preparation.

5. The preparation of claim 1 wherein the pharmaceutical active ingredient is capable of releasing no more than 50% of the pharmaceutical active ingredient in the first five hours following oral administration.

6. A controlled, slow release, solid preparation comprising 600 mg of buflomedil hydrochloride, 25 to 150mg of sodium-calcium alginate, 160 to 400 mg sodium alginate and lubricating and binding agents as needed.

7. The preparation of claim 6 comprising 80 mg of sodium-calcium alginate, 160 mg of sodium alginate, 4–5 mg of magnesium stearate and 30 mg of povidone.

8. A solid slow release preparation comprising 4 to 6 mg of tulobuterol hydrochloride, 75 to 400 mg of sodium-calcium alginate, 75 to 400 mg sodium alginate and lubricating, binding and bulking agents as needed.

9. The preparation of claim 8 wherein said lubricating agent is magnesium stearate, said binding agent is povidone and said bulking agent is lactose.

10. The process for the production of a controlled, slow release pharmaceutical preparation, said process comprising blending in the presence of water, sodium alginate, sodium-calcium alginate, a therapeutically effective amount of at least one pharmaceutically active ingredient and binders, lubricants and bulking agents as needed; and then forming the resultant preparation into a tablet.

* * * * *